United States Patent [19]

Frechette et al.

[11] 4,111,036

[45] Sep. 5, 1978

[54] PIEZOELECTRIC PROBE FOR DETECTION AND MEASUREMENT OF GASEOUS POLLUTANTS

[75] Inventors: Michael W. Frechette, Lowell, Mass.; James L. Fasching, Narragansett, R.I.

[73] Assignee: The Board of Regents for Education of the State of Rhode Island, Providence, R.I.

[21] Appl. No.: 492,737

[22] Filed: Jul. 29, 1974

[51] Int. Cl.$^2$ .......................................... G01N 31/06
[52] U.S. Cl. ...................................................... 73/23
[58] Field of Search ............. 73/23; 23/232 R, 232 E, 23/254 R, 254 E; 310/8, 8.1, 8.9

[56] References Cited

U.S. PATENT DOCUMENTS

| | | | |
|---|---|---|---|
| 3,164,004 | 1/1965 | King | 73/23 |
| 3,260,104 | 7/1966 | King | 73/23 |
| 3,327,519 | 6/1967 | Crawford | 73/23 |
| 3,329,004 | 7/1967 | King | 73/23 |
| 3,385,100 | 5/1968 | Michael | 73/23 |
| 3,534,585 | 10/1970 | Webb | 73/23 X |
| 3,677,066 | 7/1972 | King | 73/23 |
| 3,744,296 | 7/1973 | Beltzer | 73/23 |
| 3,879,992 | 4/1975 | Bartera | 73/23 |

*Primary Examiner*—Stephen A. Kreitman
*Attorney, Agent, or Firm*—Thompson, Birch, Gauthier & Samuels

[57] ABSTRACT

A new static system for the detection and measurement of gaseous air pollutants such as sulfur dioxide using a coated piezoelectric crystal is disclosed. The system is rugged, portable and inexpensive. It is readily adapted for automatic, periodic, multiple-component monitoring of an industrial exhaust stream. Also disclosed are materials especially suitable for coating the piezoelectric crystals of the present invention.

9 Claims, 3 Drawing Figures

PIEZOELECTRIC PROBE FOR DETECTION AND MEASUREMENT OF GASEOUS POLLUTANTS

BACKGROUND OF THE INVENTION

The present invention relates generally to a method and apparatus for detecting and measuring gaseous air pollutants such as those found in industrial exhaust streams from furnaces and the like. An increasing awareness of the hazards of air pollution in recent years has led to strict controls on a local and national level both in the United States and abroad over exhausting sulfur oxides, nitrogen oxides, and other inorganic and organic gases to the atmosphere. While great attention has been focused on economical means for removing these contaminants, somewhat less notice has been given to the concomitant problem of monitoring effluent gas streams to initially detect a pollution problem and, subsequently, to insure that emission abatement systems are operating properly. Conventional analytical techniques such as gas chromatography and colorimetric procedures have proven cumbersome and inadequate in accurately measuring gaseous contaminants present in concentrations on the order of a few parts per million or less; thus, new systems have been sought.

DESCRIPTION OF THE PRIOR ART

U.S. Pat. No. 2,898,243 discloses that the resonant frequency of quartz crystals can be adjusted by contacting the crystals with certain inorganic salts. The object of this invention is to produce crystals having a predetermined frequency. However, based on this concept, U.S. Pat. No. 3,164,004 teaches that a piezoelectric crystal coated with a substrate selectively sensitive to changes in the atmospheric environment can serve as a detection device in fluid analyzers. In general, this discovery is based on the principle that the oscillation of a crystal, both in frequency and amplitude, is in part a function of its weight. The change in weight of a crystal coated with a substrate selectively sensitive to a particular contaminant when placed in an environment containing that contaminant is, in turn, at least partly a function of the concentration of the contaminant. Therefore, a measuremenrt of the change in oscillation characteristics of a coated crystal sensitive to a particular contaminant upon exposure to a given atmosphere is a direct and highly sensitive measure of the presence and concentration of that contaminant. Variations of and improvements in this basic method are shown in U.S. Pat. Nos. 3,194,053; 3,260,104; 3,266,291; 3,327,519; 3,329,004, 3,385,100; 3,677,066; and 3,744,296.

All of the detection systems of the aforementioned patents are "flow" systems; that is, a sample must be taken from the gas stream which is to be analyzed and injected as a "slug" into a separate stream of carrier gas passing through the detection apparatus. Many disadvantages are inherent in these systems. In addition to the analytical apparatus per se, it is necessary to provide a secondary system comprising a source of carrier gas, controls for monitoring the flow rate of the carrier gas, and means for disposing of the contaminated carrier gas. It is necessary to periodically remove samples from the effluent gas stream and inject them into the secondary system for testing purposes if periodic monitoring of the gas stream is desired. These factors render it almost impossible to package the flow systems in portable assemblies and make automation of the monitoring process difficult. Automation is particularly desirable yet made especially difficult with prior art systems when more than one contaminant is to be simultaneously monitored since a separate secondary system including a crystal with a suitable substrate and a carrier gas must be provided for each such contaminant. Moreover, many potential sources of measuring error are introduced by the prior art systems, for example the size of the test sample injected and the flow rate of the carrier gas.

OBJECTS OF THE INVENTION

Accordingly, it is the primary object of the present invention to provide a "static" system for the detection and measurement of gaseous contaminants using a coated piezoelectric crystal.

It is also an object of the present invention to provide an apparatus for detecting and measuring gaseous contaminants which is rugged, portable yet highly accurate.

It is another object of the present invention to provide a detection and measuring system which is readily adapted for automatic, periodic, multiple-component monitoring of a gas stream.

It is a further object to provide a material especially suitable for coating the piezoelectric crystals used in the analytical system of this invention.

Further objects and advantages of this invention will become apparent as the following description proceeds with reference to the drawings.

DESCRIPTION OF THE PREFERRED EMBODIMENT

Basically, the piezoelectric detector of the present invention comprises an electronic oscillator and a probe having a vibrating piezoelectric crystal which when coated with an appropriate substrate can selectively sorb a gaseous contaminant from an effluent gas stream. The change in frequency of the crystal can be measured and directly related to the concentration of the gaseous contaminant. The change in frequency of the vibrating crystal is correlated to the weight change of the crystal according to the Sauerbrey Equation as follows:

$$\frac{\Delta F}{F} = -\frac{(F)(m)}{(D)(A)(N)} \quad (1)$$

where, $\Delta F$ = change in frequency due to coating (hz)
$F$ = frequency of uncoated crystal (mhz)
$m$ = mass of coating or substrate (grams)
$A$ = area of crystal coated (cm$^2$)
$N$ = frequency constant for crystal
$D$ = density of crystal Since, $$\frac{F}{D} = \frac{1}{T}$$

where T = thickness of the crystal, one can substitute values for F and D and determine N for quartz crystals, for example to obtain a reduced form of Sauerbrey's equation for quartz as follows:

$$\Delta F = -0.38 \times 10^6 \times \frac{F}{T} \times \frac{\Delta m}{A} \tag{2}$$

where $\Delta m$ = the weight increase of the crystal due to sorption of the gaseous contaminant.

Figure 2:
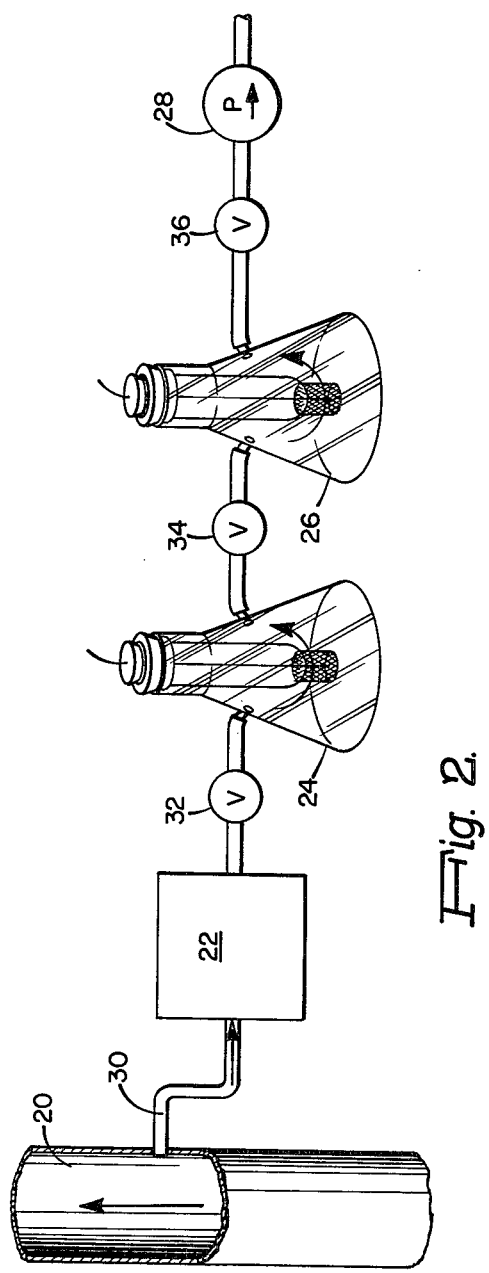
FIG. 2 is a schematic diagram of two piezoelectric probes in sample chambers connected in series to a gas conduit.
Figure 1:
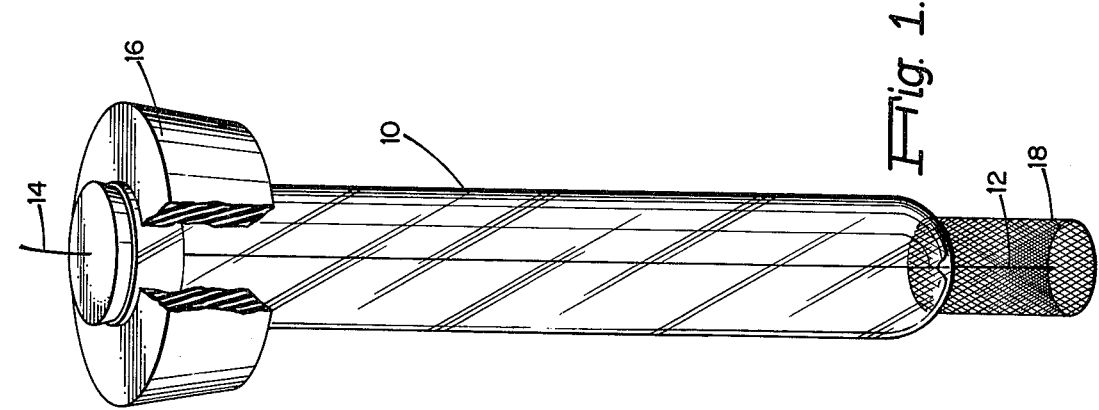
FIG. 1 is a schematic diagram of a piezoelectric probe.

FIG. 1 illustrates one easily constructed type of piezoelectric probe according to the present invention. The probe comprises a glass tube 10, which serves as a rigid support for the coated piezoelectric crystal 12 sealed by suitable means to the rounded end of the tube. The opposite end of the tube is sealed with a stopper fitted tightly through the center with a lead wire 14, one end of which is connected to the crystal 12 and the other end going to the oscillator (not shown). The tube 10 is fitted on the outside with a rubber jacket 16 so as to form a tight seal when inserted into a sample chamber as illustrated in FIG. 2. The coated crystal is preferably encased by a small, non-reactive cage 18 to protect it from mechanical damage or physical shock.

SELECTION OF PIEZOELECTRIC CRYSTAL

The piezoelectric crystal 12 is selected from among certain crystalline materials which are said to exhibit the piezoelectric phenomenon. That is, when the crystal of the substance is subjected to a mechanical stress, electrical charges build up on the surface of the substance. These charges reverse their polarity if the direction of mechanical stress is reversed. This is termed the direct piezoelectric effect and materials which exhibit this effect are called piezoelectric crystals.

Conversely, when a piezoelectric crystal is placed in an electric field, that is, electrical charges are applied to the surface, the crystal is mechanically deformed. Similarly, when the electrical potential is reversed the direction of mechanical deformation is reversed. This phenomenon is often termed the converse piezoelectric effect.

Many crystals have been qualitatively shown to exhibit the piezoelectric phenomenom. Of the 32 symmetry classes of crystals which exist in nature, 21 classes have no point of symmetry. Of these 21 classes, 20 have been shown to display piezoelectricity. Somewhat over 1000 materials have been found to demonstrate this behavior. Probably the most common are quartz, Rochelle salt ($KNaC_4H_4O_6 4H_2O$), ammonium diphosphate ($NH_4H_2PO_4$), potassium diphosphate ($KH_2PO_4$), barium titanate ($BaTiO_3$) and tourmaline.

The piezoelectric constants (those factors which describe the stress and strain of the crystals) vary considerably, since very often small amounts of impurities have large effects on these constants. The stress and strain constants of most piezoelectric materials also change markedly with temperature. Quartz has proven to be superior in this regard by demonstrating little variation in its piezoelectric constant, which is one of the reasons it is often used to make stable oscillators. Another advantage is that quartz can be used as a piezoelectric material up to about 573° C, whereas barium titanate, for instance, loses its piezoelectric properties at 120° C, and Rochelle salt melts at 55° C.

Tourmaline is also known to exhibit piezoelectricity. However, in addition to its piezoelectric behavior, tourmaline also exhibits a pyroelectric behavior; that is, when subjected to a temperature change, it becomes electrically polarized. Although the piezoelectric strain constant for tourmaline is more than fifty percent greater than that of quartz (thus it is a more sensitive piezoelectric material), the shortcomings due to these temperature effects limit its utility in the present invention. Thus, quartz crystals are preferred in the practice of this invention.

Besides different materials having different piezoelectric properties, a single material can have very different properties depending on how it is "cut". The directions in which compression and tension develop polarization parallel to the strain are called the piezoelectric axes of the crystal. For example, a quartz plate cut with the crystal faces perpendicular to the Z-axis is said to be Z-cut. A variety of stresses and strains can be produced in crystals from different combinations of the applied field and crystal orientation. AC-cut ($\theta = -90°$, $\phi = 59°$, $\gamma = 90°$) quartz crystals, for instance, exhibit large temperature coefficients, on the order of hundreds of hertz per degree, making them difficult to use in the present invention. On the other hand, AT-cut (+35° 15') quartz crystals have very low temperature coefficients and thus are ideally suited for the practice of this invention.

SELECTION OF SUBSTRATE

The selection of a suitable substrate depends foremost on the particular gaseous contaminant to be monitored. In detecting and measuring sulfur dioxide, for example, it is possible to sorb $SO_2$ with a substrate comprising a large variety of amines and amine-derivatives including the lower alkyl amines such as triethyl amine, various aromatic amines, aniline, quinoline, pyridine, toluidine, and the like. The polyamines, in general, have been found especially suitable. However, there are important factors in addition to the ability of a substrate to sorb the particular gas which lead to a preference of certain substrates over others. The three most important additional considerations are the properties of bleed, fatigue, and selectivity as discussed further below.

"Bleed" is used to describe the tendency of crystals exposed to gas streams to gradually lose their coating or substrate by evaporation and/or sublimation. The "bleed" rate is not only a function of temperature and the vapor pressure of the substrate, but also depends on the relative affinity of a particular crystal material for a particular coating. "Bleed" is a particularly important factor in the prior art "flow" systems where the coated crystal is exposed to a continuous flow of fresh carrier gas during the testing interval. Thus, one distinct advantage of the "static" systems of the present invention is the minimization of "bleeding" because the coated crystal is exposed to a smaller volume of a stationary gas.

"Fatigue" relates to the ability to regenerate and reuse a coated crystal without the need for recoating it. Although many substrates can be found which will selectively and irreversibly sorb a gaseous component from a gas stream, it is not convenient or economical to operate the system in this manner. It is preferred to employ a substrate which will sorb a gaseous component when exposed to an atmosphere containing the same and will desorb or flush the component when removed from the contaminated atmosphere. Often the desorption or flushing is promoted by raising the temperature of the crystal and substrate to a point where the physical and/or chemical bonds between the substrate and the sorbed gas are broken thereby freeing the gas and regenerating the substrate.

Even among the various substrates which are considered "reversible", none is capable of being completely regenerated. This is believed to be due to the irreversible occupation of certain active sites on the substrate surface by molecules of sorbed gas. The important factor in fatigue studies of substrates, however, is the reproducibility of the results. It is preferable to select a substrate which, at least after several cycles, is dependably regenerable to, for example, 70% of its original sorption capacity as compared with one which shows increasing fatigue on subsequent cycles. The process of subjecting a coated crystal to one or more sorption-desorption cycles before actual use is termed "conditioning". It has been found that a conditioning process is helpful in reducing detector fatigue. After the coating is applied to the crystal surface, the crystal is placed, for example, in a sulfur dioxide-containing gas stream and allowed to sit for approximately 30 minutes. In this procedure it appears that the more active surface sites become covered, so that less fatigue is experienced with subsequent sampling.

It will be readily appreciated that fatigue plays a more critical role in a portable system where it is desirable to reuse a crystal detector several times before recoating it. Since each recoating of the crystal necessitates "reconditioning" the crystal to reach a constant regenerating capacity and then recalibrating the other instruments according to the new crystal weight, the need for frequent recoating would defeat the objects of portability, economy, and adaptability to automation.

Finally, for a portable system it is especially important to consider the selectivity of a substrate for a particular gas and the degree to which the substrate is subject to interferences by other gases. It should be apparent that if a substrate sorbs not only the gas being detected and measured but another component gas of the gas stream as well, the frequency change in the crystal will reflect the joint sorption and yield misleading results. This problem can be minimized in the prior art systems by separating the interfering gas from the sample, for instance by gas chromatography, prior to injecting the sample into the analyzer apparatus. Obviously, such a separation is not possible with the portable "static" systems of the present invention. Accordingly, it is necessary to select a substrate for the present invention based upon a consideration of all of the components of the gas stream which is to be monitored.

It has now been found that for the purposes of the present invention, two polyamines identified herein as SDM polymer and PP-2040 are preferred substrates for quartz crystals in the detection and measurement of sulfur dioxide.

SDM polymer is a 1:1 copolymer of styrene and N,N dimethylaminopropyl maleimide manufactured by Uniroyal, Inc. of Middlebury, Connecticut under one or more of the following U.S. Pat. Nos. 3,659,009; 3,652,734; 3,652,198; 3,560,590; 3,502,422; 3,485,574; 3,439,999; 3,432,250; 3,399,251; and 3,361,843. Essentially, the structural formula for SDM polymer is:

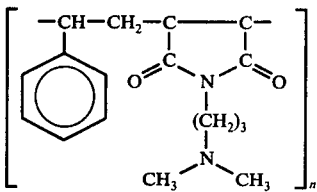

It is a crystalline material and is easily soluble in acetone and many other volatile solvents.

PP-2040 is a copolymer of 2-vinyl and 2-methyl, 5-vinyl pyridines manufactured by the Ionac Chemical Corp., Birmingham, New Jersey and having the following general structural formula:

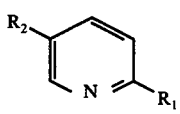

wherein $R_1$ is a vinyl or methyl group and $R_2$ is a vinyl group or hydrogen.

In the detection and measurement of nitrogen dioxide, for example, cellulose nitrate are cellulose acetate have been found to work well as substrates. Tri-chloro methane has been detected with a substrate of "Carbowax 20M". It is understood that the above enumeration of gaseous contaminants and suitable substrates therefor is only exemplary, and the present method and apparatus is not limited thereto. The invention is applicable to any gaseous contaminant except for the inert gases and to any corresponding substrate materials which meet the requirements set forth above.

COATING OF CRYSTALS

The piezoelectric crystals of this invention may be coated with substrate in any conventional manner depending on the nature of the substrate. The quantity of substrate applied must be kept relatively small in comparison with the weight of the crystal since large quantities of substrate would completely "damp" the vibration of the crystal. In general, the substrate is a solid organic compound. The easiest method for depositing this type of substrate on a crystal in a thin, uniform layer is by dissolving the substrate in a readily-volatilized solvent, applying a small drop of the solution to the crystal surface with a microliter syringe, and, optionally, applying an infrared lamp to the crystal to hasten the evaporation of the solvent.

The amount of substrate applied to a crystal will typically vary from about 1–50 micrograms/cm.$^2$ based on the surface area of the crystal. Since the frequency of the crystal both before and after coating can be readily measured, the actual weight of substrate applied to the crystal can be determined from the Sauerbrey equation as discussed above.

One of the problems encountered in laboratory testing of the present invention is that the coated piezoelectric crystals are so sensitive to gaseous contaminants that at relatively high concentrations of the gas, for example 1000 ppm. and larger, the substrate seems to become saturated producing unpredictable results. For instance, quartz crystals coated with SDM polymer perform most reliably in the detection and measurement of SO$_2$ concentrations below about 300 ppm. One method of adapting the present apparatus for the analysis of higher gas concentrations is to simply use a less sensitive substrate. However, it is often preferred to work with a single type of substrate, the properties of which are well known in a particular application. Thus, an alternative coating method resulting in a less sensitive crystal is to disperse the "active" coating on the crystal surface in some inert matrix. "Carbowax 6000" was found to be a particularly suitable dispersing medium for SDM polymer and PP-2040 in $SO_2$ detection. It was selected on the basis of its high solubility in a variety of easily-volatilized solvents, formation of a smooth coating on the crystal, and its complete inertness toward sulfur dioxide.

DETECTION OF CONTAMINANT GASES

FIG. 2 is a schematic diagram illustrating the use of the piezoelectric probe of FIG. 1 in the detection and measurement of two contaminant gases according to the present invention. Conduit 20, which may be for example a smoke stack, carries the main gas stream. The detection system illustrated includes a water-removal device 22, as hereinafter described, two sample chambers 24 and 26, and a small pump 28, all connected to conduit 20 by side conduit 30. Initially the sample chambers, which conveniently are fashioned from Erlenmeyer flasks, are sealed with a thin, breakable plastic membrane or diaphragm such as cellophane. When a measurement is about to be made, stop-cocks or valves 32,34, and 36 are opened, and the pump 28 is used to draw a portion of the main gas stream through the detection system. When all of the air has been flushed from the system, the stop-cocks are closed and piezoelectric probes with suitable substrates are thrust through the plastic diaphragms into the sample chambers. Readings are made when essentially steady-state oscillation conditions are attained. After the readings are taken, the probes are removed for regeneration of the substrate, and the sample chambers are again sealed.

Figure 3:
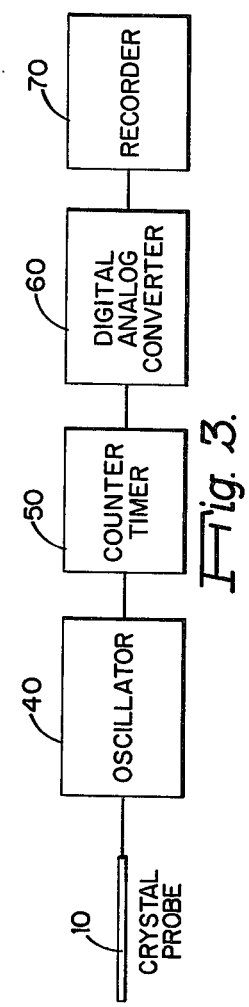
FIG. 3 is a block diagram of the static analyzer system.

FIG. 3 is a block diagram illustrating the analyzer components of the "static" system. The analyzer components include the piezoelectric probe 10 associated with one or more sample chambers, an electric oscillator 40 to vibrate the coated crystal, a counter-timer 50, a digital analog converter 60, and a recorder 70.

One type of oscillator for driving the crystal is an International Crystal Corporation Model OT-3 transistorized circuit with a frequency range of 2.0–12.0 MHz. The circuit is mounted in an International Crystal Corporation Model FOT-10 case which also contains a battery (9v) and an on-off switch. The crystal is electronically connected to the oscillator with shielded cable to protect the system from stray electrical noise.

The electrical signal from the oscillator 40 is sent to a counter-timer 50. One type of counter-timer is a Monsanto Model 101-A Counter-Timer, which gives a visual display of the crystal frequency. The counter has a frequency range of 5–12.5 MHz with a maximum resolution of a tenth of a hertz and an accuracy of ±1 count. It has the capability of displaying any five consecutive digits anywhere in the frequency range. However, with this apparatus, the smaller the frequency change which is observed, the longer is the time interval (gate time) between displays. A resolution of 1 Hz has been found to be a practical sensitivity and has a fast enough gate time to provide an essentially continuous monitor of crystal frequency.

A Monsantor Model 503-A Digital-Analog Converter is used in conjunction with the counter-timer to provide a permanent record of each sample trace. The converter can process any three consecutive digits selected from the counter-timer output. It has an output of 100 millivolts at a maximum reading of 999.

The recorder generally comprises a rotating drum covered with graph paper and a pen for continuously redording the frequency response of the crystal. One type of apparatus for recording the analog trace from the digital-analog converter is a Speedomax H recorder (Leeds and Northrup) with a 0–10 millivolt range, a chart speed of 60 inches per hours and a one second response time. A Tech Lab Incorporated Type 600 attenuator is used with the digital-analog converter and the recorder to match the output signal.

The method and apparatus of the prior art tend to produce the bell-shaped curves familiar in gas chromatography because once the portion of carrier gas containing the sample slug passes the detector the coating begins to desorb the gaseous component which is then flushed from the system. By contrast, the present invention produces a recorder readout which is an S-shaped curve representing a gradual increase in crystal weight as the gaseous component is sorbed by the substrate until essentially steady-state conditions are reached and the curve levels out.

When a gas stream is to be monitored for two or more contaminant gases as illustrated in FIG. 2, a crystal probe as illustrated in FIG. 1 is prepared for each gas to be monitored. Depending on the particular gas, each crystal is coated with a suitable substrate as heretofore described. Each probe is then connected to the electric oscillator and the measuring-recording system. By means of suitable apparatus, the probes may be sequentially rotated into the sample chambers, then removed and regenerated for reuse. The length of time that each probe remains in a sample chamber may be pre-set manually. Alternatively, in the preferred embodiment, the apparatus is automated so that each probe remains in the conduit only until essentially steady-state conditions are obtained. Steady-state conditions may be conveniently defined for example, as the point at which a crystal demonstrates a decreasing frequency change of less than 10% per minute based on the net frequency change for the last previous measurement, that is when the S-shaped graph begins to level-off.

It has been found that the presence of large amounts of water vapor on the order of 1000 parts per million in the gas streams are detrimental to the performance of the detectors of this invention. The coating or substrate is soon deactivated by excessive water after which useful responses cannot be obtained. Several water-removal techniques may be used to surmount this obstacle.

The apparatus which has been found suitable for removing excessive moisture and which may serve as the water-removal device 22 shown in FIG. 2 includes columns packed with a water-sorbent material such as Drierite, molecular sieves, and Chromosorb 101, and "freezing traps" to freeze-out water vapor. A typical freezing trap in accordance with the present invention comprises a glass tube with ground glass fittings and packed with 6 mm. glass beads to provide an increased surface area for contact with the side stream. The packed tube or column is immersed in an ice-salt freezing mixture at a temperature of about −15° C.

The internal volume of the sample chambers is not critical, but in general it has been found advantageous to use larger sample chambers for measuring smaller concentrations of contaminant gases and smaller chambers for measuring higher gas concentrations. Although the detector response increases almost linearly with sample chamber volume, there is a corresponding increase in the time required for the detector to reach a stable frequency readout. Thus, to optimize these parameters, the sample chamber should be of such a size that a determination can be made as rapidly as possible yet still produce an easily detectable response. It has been found that a sample chamber of about 30 cm.$^3$ is suitable for detecting SO$_2$ concentrations on the order of 300 ppm. While smaller concentrations on the order of 30 ppm. require a larger sample chamber of about 120 cm.$^3$ to obtain a suitable response.

The present invention will be further described by reference to the following examples.

EXAMPLE 1

The purpose of this example was to compare the responsiveness of different substrates at different gas concentrations and substrate weights in detecting and measuring sulfur dioxide. Quartz crystals were coated with the substrates, and the crystal frequency was measured both before and after coating to obtain the frequency change due to the substrate alone ($\Delta F_{subs}$). The coated crystals were then employed in "flow" systems where they were exposed to atmospheres containing sulfur dioxide and again the frequency change, this time due to sorption of SO$_2$ ($\Delta F_{SO_2}$) was determined.

The sorption detector system was constructed as shown in FIG. 3. The oscillator used in this study was an International Crystal Corporation Model OT-3 9-MHz circuit. A Monsanto Model 101A Counter Timer and a Monsanto Model 503A Digital-Analog Converter were used along with a Speedomax H Recorder (Leeds and Northrup) for visual display of the output signal. Two different sample cells were used, cell 1 having a 2 cm.$^3$ internal volume, while cell 2 had a 0.10 cm.$^3$ volume. Initially cell 1 was used in this study, but it was soon determined that a cell with a smaller internal volume would be more sensitive. A decrease in the dilution of the sample with the gas stream would allow a higher concentration of the SO$_2$ to interact with the applied coating in a given time interval. Samples of pure SO$_2$ were injected through a silicone rubber septum using gas tight syringes or alternatively through a gas sampling value arrangement. Because of variations in the parameters in the system, all of the data were "normalized" using the following equation:

$$\Delta F_{SO_2} \times \frac{5000}{\Delta F_{subs}} \times \frac{0.1}{\text{Sample}} = \Delta F^*_{SO_2}$$

where $\Delta F^*_{SO_2}$ = adjusted $\Delta F_{SO_2}$, $\Delta F_{SO_2}$ = frequency change due to SO$_2$, $\Delta F_{subs}$ = frequency change due to applied substrate, sample size = cm.$^3$ of sample injected. The value $\Delta F^*_{SO_2}$ was found to be a good relative measure of the responsiveness of a substrate. The data are presented in Table 1 below:

Table 1

| Relative SO$_2$ Response for evaluated Substrates | |
|---|---|
| Cell 1 | $\Delta F^*_{SO_2}$ |
| Tridodecyl amine | 160. |
| Melamine | 4. |
| Diallyl Melamine | 24. |
| Igepal CO-880 (Appli. Sci. Lab.) | 69. |
| Cellulose nitrate | 35. |

Table 1-continued

| Relative SO$_2$ Response for evaluated Substrates | |
|---|---|
| Diallyl amine | 70. |
| Cell 2 | |
| Phenyldiethanolamine | 150. |
| UC-W98 (Appli. Sci. Lab.) | 45. |
| Versamid 900 (Appli. Sci. Lab.) | 50. |
| PP-2040 (Ionac Chem. Co.) | 190. |
| PE-100 (Ionac Chem. Co.) | 68. |
| Tripropyl amine | 225. |
| 2,2-(m-tolylimino)diethanol | 3. |
| SDM polymer (UniRoyal) | 195. |

This example demonstrates the relatively high responsiveness of SDM polymer and PP-2040 polymer as substrates in the detection of SO$_2$.

Another important factor is the variation in the response characteristics of a substrate at varying gas concentrations. In general, the ratio $\Delta F_{SO_2}/\Delta F_{subs}$ varies directly with both the weight of the substance (measured by $\Delta F_{subs}$) and the concentration of sulfur dioxide in the gas stream. The variation of detector responsiveness with changes in the concentration of sulfur dioxide is a disadvantage in the present invention because this factor makes it difficult to measure high and low concentrations of sulfur dioxide with the same coated crystal. However, SDM polymer, and PP-2040 to a lesser extent, demonstrate distinctly non-linear responsiveness characteristics with decreasing SO$_2$ concentrations. In plotting the graph of the ratio ($\Delta F_{SO_2}/\Delta F_{subs}$) as a function of SO$_2$ concentration for SDM polymer, it was found that the decrease in substrate responsiveness rapidly levels off at concentrations below about 500 ppm. So that at concentrations as low as 30 ppm., detector responsiveness is still better than 0.0100. This is true even for readings taken at a relatively low substrate weight (for example $\Delta F_{subs}$ = 3800 Hz). As heretofore discussed, it is important to be able to obtain a suitably large response with a relatively small amount of substrate in comparison with the weight of the crystal since too much substrate tends to damp out the vibrations of the crystal.

On the other hand, a high responsiveness at low substrate weights is not by itself an adequate criterion to evaluate substrates for this invention. The response data for tridodecyl amine, phenyldiethanolamine, and tripropyl amine shown in Table 1 suggest that these materials would be highly desirable substrates for SO$_2$ detection. However, the following examples relating to "bleed" and fatigue properties demonstrate the overall superiority of SDM polymer and PP-2040 as substrates for the present invention.

EXAMPLE 2

The purpose of this example was to compare the "bleed" characteristics of different substrates in the detection and measurement of sulfur dioxide. Quartz crystals were coated with the different substrates being compared, and each was, in turn, exposed to a gas stream containing a carrier gas of either helium or nitrogen. Any changes in the frequency readings were attributed to a loss of substrate by "bleeding", and this serves as a convenient measure of "bleed" rates. The results are tabulated in Table 2 below:

Table 2

| Substrate | Bleed Rate Hz/min. |
|---|---|
| SDM poly,er | less than 0.5 |
| Versamid 900 (polyamidoamine resin) | less than 0.5 |

Table 2-continued

| Substrate | Bleed Rate Hz/min. |
|---|---|
| UC-W98 (methyl silicone gum) | less than 0.5 |
| Polyethyleneimine | 3 |
| PE-100 (cationic polyelectrolyte) | 3 |
| PP-2040 (methyl vinyl pyridine copolymer) | less than 0.5 |

In addition, some of the non-polymeric materials tested as substrates demonstrated bleed rates as high as 100 Hz/min.

It is thus seen that SDM polymer and PP-2040 have very low "bleed" rates on the order of 0.5 Hz/min. or less. Polyethylemeimine, a highly-responsive substrate, demonstrated an undesirably high "bleed" rate of 3 Hz/min., six times that of SDM polymer and PP-2040.

EXAMPLE 3

The purpose of this example was to compare the "fatigue" characteristics of different substrates in the detection and measurement of sulfur dioxide. Quartz crystals were coated with the different substrates being compared, and each was, in turn, subjected to two or more "exposure cycles". Each exposure cycle consisted of placing the coated crystal in a gas stream containing sulfur dioxide until essentially steady-state conditions were reached, recording the crystal frequency, desorbing the sulfur dioxide by flushing the crystal with gas free of sulfur dioxide until essentially steady-state conditions were reached, and recording the new base frequency. For each cycle, the value of $\Delta F_{SO_2}$ was determined by substracting from the base frequency at the end of the preceding cycle the frequency of the coated crystal when equilibrium with the new $SO_2$-containing gas stream has been established. The decrease in the value of $\Delta F_{SO_2}$ is important primarily as it effects the responsiveness of the detector, the ratio $(\Delta F_{SO_2}/\Delta F_{subs})$ was again used as the basis for comparison among different substrates. It should be noted at this point that although the base frequency used in determining $\Delta F_{SO_2}$ for each cycle may vary, $\Delta F_{subs}$ representing the frequency change due to substrate alone is constant throughout each set of tests (except for changes due to "bleed" which were not taken into account in view of the relatively short testing period). The results of this test for SDM polymer are shown in Table 3 below:

Table 3

| SDM Substrate Sample # | Cycle # | $\Delta F_{subs}$ Hz | $\Delta F_{SO_2}$ Hz | $\Delta F_{SO_2}/\Delta F_{subs}$ | Conc. $SO_2$ ppm. |
|---|---|---|---|---|---|
| 1 | 1 | 5796 | 345 | .0595 | 30 |
|   | 2 | 5796 | 264 | .0455 | 30 |
|   | 3 | 5796 | 269 | .0465 | 30 |
|   | 4 | 5796 | 263 | .0454 | 30 |
|   | 5 | 5796 | 267 | .0461 | 30 |
| 2 | 1 | 3875 | 153 | .0395 | 30 |
|   | 2 | 3875 | 145 | .0374 | 30 |
|   | 3 | 3875 | 149 | .0384 | 30 |
|   | 4 | 3875 | 148 | .0382 | 30 |
|   | 5 | 3875 | 149 | .0384 | 30 |
| 3 | 1 | 2800 | 127 | .0454 | 30 |
|   | 2 | 2800 | 106 | .0379 | 30 |
|   | 3 | 2800 | 128 | .0457 | 30 |
|   | 4 | 2800 | 124 | .0442 | 30 |
|   | 5 | 2800 | 122 | .0436 | 30 |
|   | 6 | 2800 | 120 | .0429 | 30 |
| 4 | 1 | 625 | 26 | .0416 | 30 |
|   | 2 | 625 | 28 | .0448 | 30 |
|   | 3 | 625 | 26 | .0416 | 30 |
|   | 4 | 625 | 29 | .0464 | 30 |
|   | 5 | 625 | 26 | .0416 | 30 |

Although all of the samples tested have some tendency to "fatigue" with repeated sampling, SDM polymer shows a rapid leveling-off of fatigue after one or two cycles, and subsequent cycles demonstrate little change in the responsiveness of the substrate. This indicates that SDM polymer-coated crystals can be easily "conditioned" by one or two cycles of pre-testing exposure to sulfur dioxide-containing atmospheres to obtain reliable detectors retaining 80% or better of their original responsiveness. By contrast, tridodecyl amine and polyethyleneimine, two substrate materials which have a high initial responsiveness, were found to fatigue rapidly dropping to one-quarter or less of their original responsiveness after only a few cycles.

EXAMPLE 4

The purpose of this example was to compare the extent to which different substrates were subject to interference by the presence of other gases commonly found in stack effluents in the detection and measurement of sulfur dioxide.

Probably the most common of these gases, and the most serious, are the nitrogen oxides. Nitrous acid, formed by reaction of nitrogen dioxide and water, reacts with amines resulting either in deamination via diazonium salt formation or in formation of nitroso compounds. Primary amines react as follows:

$$RNH_2 + HNO_2 \rightarrow R-N \equiv N+$$

while aryl primary amines react as follows:

$$ArNH_2 + HONO \rightarrow Ar-N \equiv N+$$

Both alkyl and aryl secondary amines result in the formation of N-nitrosoamines as follows:

$$R-NH-R + HONO \rightarrow R_2N-N=O$$

$$Ar-NH-R + HONO \rightarrow Ar-NR-N=O$$

Tertiary amines produce compounds according to the following mechanisms:

$$R_3N + HONO \rightarrow R_2N-N=O + \text{aldehydes} + \text{ketones}$$
$$Ar-N-R_2 + HONO \rightarrow \text{p-nitroso compound}$$

In general, tertiary amines do not undergo these reactions, although long exposure to nitrogen dioxide may damage the amine coating.

Nitric oxide has also been reported to react with amines by the following scheme:

$$R_2NH + NO \rightarrow R_2NHNO$$

$$R_2NH-NO + NO \rightarrow R_2NHN_2O_2 \rightarrow \text{complex ion}$$

It would thus be expected that tertiary amines would make the better substrates due to their relatively low reactivity with the most common nitrogen oxides.

Other common gases present in stack effluents which could also cause chemical interference with the amine coating include the carbon oxides and the other nitrogen oxides. Both CO and $CO_2$ are generally considered to be unreactive and possess very different electronic structures than sulfur dioxide. The electronic structure of sulfur dioxide, represented by a resonance hybrid, has a +1 formal charge on the sulfur atom and a −1 formal charge on one of the oxygen atoms. The sulfur atom is seeking to eliminate the charge and can do so by forming a charge transfer complex with an amine. Carbon dioxide, on the other hand, cannot react in this way, since it would be going from a zero formal charge to a charged complex on interaction. Carbon monoxide generally acts as a Lewis base, and, since it is isoelectronic with nitrogen, it should display similar unreactive properties.

Nitric oxide, in itself, would not be expected to present an interference problem since in the presence of oxygen it is immediately converted to nitrogen dioxide ($NO_2$) viz:

$$2NO + O_2 \rightarrow 2NO_2$$

Nitrous oxide (laughing gas, $N_2O$), occurs as a resonance hybrid and is extremely unreactive.

Nitrogen dioxide, besides forming nitrous acid as heretofore described, has a very similar electronic structure to sulfur dioxide as illustrated below. Since it also acts as a Lewis acid, it would be expected to present the most serious interference.

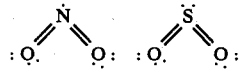

Experimentally, the responses for the different gases mentioned were found to agree very well with the predictions. The carbon oxides presented no interference porblem, having essentially a zero response for both the SDM polymer and PP-2040. In fact, gas blends of sulfur dioxide in air or nitrogen showed no different a response than similar blends made in carbon dioxide. As expected, nitrogen dioxide was the prime interference found among the gases evaluated.

For this example, quartz crystals were coated with the different substrates being compared and each was, in turn, subjected to atmospheres containing, respectively, each of the different gases being tested. Comparison was made by expressing the results as a percentage of the response of each substrate for a particular gas with that for an equal concentration of sulfur dioxide.

The results are tabulated in Table 4 below:

Table 4

| Substrate | Gas | %-Response | |
|---|---|---|---|
| diallyl amine | CO | 1.37 | |
| | $CO_2$ | 0 | (no response) |
| | $NO_2$ | 45.9 | |
| cellulose nitrate | CO | 0 | (no response) |
| | $CO_2$ | 0 | (no response) |
| | $NO_2$ | 41.8 | |
| polystyrene | $NO_2$ | 27.5 | |
| polyurethane | CO | 0 | (no response) |
| | $CO_2$ | 7.55 | |
| | $NO_2$ | 68.0 | |
| | air | 1.89 | |
| SDM polymer | CO | 0 | (no response) |
| | $CO_2$ | 1.0 | |
| | $N_2O$ | 0.7 | |
| | $NO_2$ | 21.0 | |
| | $N_2$ | 0 | (no response) |
| | $O_2$ | 0.1 | |
| | $CH_4$ | 0 | (no response) |
| PP-2040 | CO | 0 | (no response) |
| | $CO_2$ | 0.2 | |
| | $N_2O$ | 0.1 | |
| | $NO_2$ | 14.3 | |
| | $N_2$ | 0 | (no response) |
| | $O_2$ | 0.1 | |

Table 4-continued

| Substrate | Gas | %-Response | |
|---|---|---|---|
| | $CH_4$ | 0 | (no response) |

This example illustrates that with the exception of nitrogen dioxide ($NO_2$), none of the other gases commonly found with sulfur dioxide in effluent gas streams significantly interferes with the performance of typical $SO_2$-sorbing substrates. However, with regard to $NO_2$ interference, SDM polymer and PP-2040 are surprisingly superior in showing a lower response for $NO_2$ than other substrates tested. This selectivity between $SO_2$ and $NO_2$ is one important feature of the present invention.

EXAMPLE 5

The purpose of this example was to test the performance of the "static" piezoelectric detector of this invention at relatively high sulfur dioxide concentrations in the range of 1000–5000 ppm. A quartz crystal was coated with SDM polymer and subjected to atmospheres containing increasingly high concentrations of $SO_2$. The results of this test are shown in Table 5 below:

Table 5

| Conc. $SO_2$ (ppm.) | $\Delta F_{subs}$(Hz) | $\Delta F_{SO_2}$ (Hz) | $\Delta F_{SO_2}/\Delta F_{subs}$ |
|---|---|---|---|
| 1000 | 5274 | 410 | .0777 |
| 1000 | 5274 | 490 | .0929 |
| 2000 | 5274 | 570 | .1080 |
| 2000 | 5274 | 630 | .1194 |
| 3000 | 5274 | 725 | .1374 |
| 3000 | 5274 | 670 | .1270 |
| 5000 | 5274 | na | — |
| 5000 | 5274 | na | — |

Although the detector generally performed well at higher concentrations, the response time became exceedingly long. The slope of the analog trace became very gradual and moved slowly upward after a relatively fast initial rise. At 5000 ppm. the detector seemed to become saturated and unpredictable responses were obtained. Reproducibility from day to day also became a problem in this high concentration range. It would therefore appear that the piezoelectric detector, constructed and coated with the SDM polymer, in accordance with this embodiment of the present invention is best suited for use in the concentration range below about 1000 ppm. of $SO_2$, preferably below about 300 ppm. where the most predictable and reproducible responses are obtained. However, the use of a less-sensitive coating as hereinafter described permits the detector to be applied to the measurement of sulfur dioxide in the thousands of ppm. range.

On the other hand, the lower limit of detectability for the apparatus as herein described is about 0.1 ppm. of $SO_2$. Several things may be done to further reduce this limit. For example, the smallest frequency change that can be seen with the Monsanto 101-A counter-timer is about 1 Hz with a reasonable gate time (that is, the frequency of the read out). Counters are available with a tenth of a hertz accuracy and a gate time of 0.1 seconds. In addition, it appears that an increase in the sample chamber volume would lend greater sensitivity to the system. The use of better quality piezoelectric transducers would also increase the detector sensitivity, since the "weight-sensing" property of the quartz is the heart of the system.

EXAMPLE 6

It has been found that the substrates demonstrating the greatest responsiveness in the practice of this invention become highly sensitive at sulfur dioxide concentrations above about 1000 ppm. One method of measuring these relatively high concentrations is to simply employ a less sensitive material for a substrate. Alternatively, the sensitivity of SDM polymer can be conveniently reduced to any desired level to provide a detector for any given concentration range of $SO_2$ by the technique of dispersing the polymer to the extent of about 1-50 wt.-% in an inert matrix.

The purpose of this example was to compare the responsiveness and fatigue characteristics of substrates containing various amounts of SDM polymer. Carbowax 6000 was selected as the dispersing medium based on its desirable properties of solubility in easily volatilized solvents, formation of smooth coatings on quartz crystals, and complete inertness toward sulfur dioxide. Solid solutions of SDM polymer in Carbowax 6000 were prepared and used to coat quartz crystals which were then exposed to atmospheres containing 300 ppm. $SO_2$. The results of these tests appear in Table 6 below:

Table 6

| % SDM Polymer | $\Delta F_{subs}$ Hz | Eff. $\Delta F_{subs}$ Hz | $\Delta F_{SO_2}$ Hz | $\Delta F_{SO_2}/\Delta subs$ |
|---|---|---|---|---|
| 24.2 | 10,274 | 2486 | 323 | .0314 |
|  |  |  | 270 | .0263 |
|  |  |  | 250 | .0244 |
|  |  |  | 206 | .0200 |
|  |  |  | 155 | .0151 |
| 9.09 | 9,608 | 873 | 130 | .0135 |
|  |  |  | 111 | .0115 |
|  |  |  | 109 | .0113 |
|  |  |  | 101 | .0105 |
|  |  |  | 104 | .0108 |
| 4.76 | 9,938 | 473 | 78 | .00785 |
|  |  |  | 65 | .00655 |
|  |  |  | 57 | .00573 |
|  |  |  | 57 | .00573 |
|  |  |  | 55 | .00553 |

It can readily be seen from Table 6 that the solid solution dispersion technique is an effective method for reducing the sensitivity (as measured by the ratio $\Delta F_{SO_2}/\Delta F_{subs}$) of SDM polymer. The above tests were conducted at an $SO_2$ concentration of 300 ppm. for purposes of comparison with previous examples. As heretofore discussed, the responsiveness of crystals coated by the dispersion technique when actually used for detecting higher gas concentrations of 1000 ppm. or greater will be proportionately larger. Thus, the sensitivity of the detectors of this invention can be adjusted so that the responsiveness is great enough to provide meaningful readings without being overly sensitive to high concentrations of the contaminant gas.

In the detection and measurement of sulfur dioxide, one of the main interferences is water vapor in the effluent gas. Water interference can act in a twofold manner. It may physically condense or interact with the coating or crystal surface causing a weight increase, thus a corresponding frequency shift. In addition, water may react with sulfur dioxide forming sulfurous acid, which, in turn, may be oxidized to sulfuric acid. This can result in chemical deactivation of the coating by amine salt formation according to the following reactions:

$$H_2O + SO_2 \rightarrow H_2SO_3$$

$$H_2SO_3 + O_2 \rightarrow H_2SO_4$$

$$R_3N + H_2SO_3 \rightarrow R_3N^+H\ HSO_3^-$$

$$R_3N + H_2SO_4 \rightarrow R_3N^+H\ HSO_4^-$$

This is a particular problem in stack gas analysis since in combustion processes large amounts of water are ordinarily produced.

Therefore, when the concentration of water vapor in the effluent gas being monitored is found to be such that it is causing interference, a water-removal device as illustrated in FIG. 2 is employed. The side stream of gas is removed from the main effluent conduit and pretreated for moisture removal before being passed to the sample chamber. Although any conventional procedure for removing water vapor from a gas stream may be used, it has been found particularly advantageous to use a "freeze-out" technique. This method consists of directing the side stream of gas through a tube or container maintained at a temperature below the freezing point of water. It has been found that temperatures of about −15° C. such as are obtainable by the use of salt-ice baths are ideal for water removal. Also it has been found that packing the tube or container with glass beads to increase gas-surface contact aids in water removal.

As heretofore discussed, the present invention can be used to monitor a plurality of gases by using a different probe coated with a suitable substrate for each such gas and making individual readings for each. An alternative method also requires one probe for each gas being monitored. However, instead of selecting different gas-specific substrates, a substrate which is responsive to each of the gases being monitored is selected and coated on the different probes in varying amounts. By prior measurement the response ratio of, for example, two gases of interest can be measured at known concentrations for known substrate weights as a basis for comparison. Assuming a constant response ratio, for these parameters, a set of simultaneous equations can be formed and used to simultaneously measure the concentration of each of the two gases in a complex mixture. This same principle can be extended, i.e. four probes yields four simultaneous equations, which can be solved with the aid of a computer.

Although the present invention has been described with particular reference to detecting and measuring sulfur dioxide in industrial effluent gases, it will be readily appreciated that the process and apparatus of this invention is adaptable for use with other gases and applicable to other fields of use. By the selection of appropriate substrates, this invention may be used to detect and measure $No_2$, $CO_2$ and the chlorinated hydrocarbons for example. This invention may be used for instance, in determining the water content of fuel, $CO_2$ content in carbon analysis, $SO_2$ and $SO_3$ content in sulfur analysis, and in the analysis of various organic compounds. Additional applications for this invention will be apparent to those skilled in the art.

Having described the invention, what is claimed is:

1. An apparatus for the static detection and measurement of a sulfur dioxide component of a mixed gas stream flowing in a conduit comprising in combination:
   a. for each fluid component to be measured, a single vibrateable piezoelectric material mounted on a readily-transportable support base for contacting said piezoelectric material with said gas; substrate means coated on said piezoelectric material capable of sorbing said fluid component of said gas stream to thereby change the weight of said coated piezoelectric material, said substrate means comprising a polyamine; and, electronic oscillator means operatively connected to said coated piezoelectric material for oscillating said material;

b. means for withdrawing a portion of said gas stream from said conduit and for bringing said portion into a test chamber;
c. valve means for sealing said test chamber so as to bring said withdrawn portion of the gas stream into contact with said coated piezoelectric material under substantially static conditions; and,
d. means for determining when the change in vibrational frequency of said coated piezoelectric material is substantially complete, said determining means comprising counter-timer means operatively connected to said coated piezoelectric material, and a digital converter and a recorder operatively connected to said counter-timer means.

2. A process for periodically monitoring a mixed gas stream flowing in a conduit to detect and measure a sulfur dioxide component thereof comprising the following steps:

a. coating a single vibrateable piezoelectric material with a substrate capable of sorbing said sulfur dioxide component of said gas stream, said substrate comprising a polyamine; mounting said coated piezoelectric material on a readily-transportable support base; operatively connecting said coated piezoelectric material to electronic oscillator means for oscillating said material;
b. withdrawing a portion of said gas stream from said conduit and passing it into a test chamber;
c. sealing said test chamber by valve means so as to bring said portion of said gas stream into contact with said coated piezoelectric material under substantially static conditions; and,
d. recording the frequency response of said coated piezoelectric material until the change in vibrational frequency is substantially complete.

3. In an analyzer comprising in combination a detection device having a piezoelectric element bearing a substrate which interacts with one component of a fluid being analyzed, oscillating circuit means for oscillating said detection device, and measuring means for recording the frequency of oscillation of said detection device, the improvement which comprises employing a substrate selected from the group consisting of 1:1 copolymers of styrene and N,N-dimethylaminopropyl maleimide having the general formula

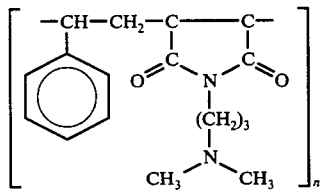

and copolymers of 2-vinyl and 2-methyl, 5-vinyl pyridines having the general formula

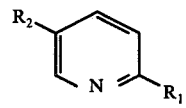

wherein $R_1$ is a methyl or vinyl group and $R_2$ is hydrogen or a vinyl group.

4. In an analyzer comprising in combination a plurality of detection devices each having a piezoelectric element bearing a substrate which interacts with one component of a fluid being analyzed, oscillating circuit means for oscillating said detection devices, and measuring means for recording the frequency of oscillation of said detection devices, the improvement which comprises employing a substrate selected from the group consisting of 1:1 copolymers of styrene and N,N-dimethylaminopropyl malemide having the general formula

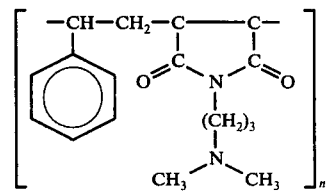

and copolymers of 2-vinyl and 2-methyl, 5-vinyl pyridines having the general formula

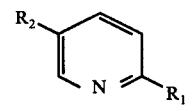

wherein $R_1$ is a methyl or vinyl group and $R_2$ is hydrogen or a vinyl group.

5. An apparatus for the static detection and measurement of a sulfur dioxide component of a mixed gas stream comprising in combination:

a. a vibrateable piezoelectric material mounted on a readily-transportable support base for contacting said piezoelectric material with said gas;
b. substrate means coated on said piezoelectric material capable of sorbing at least one of said fluid components of said gas stream to thereby change the weight of said coated piezoelectric material, wherein said substrate is a polyamine selected from the group consisting of 1:1 copolymers of stryene and N,N-dimethylaminopropyl maleimide having the general formula

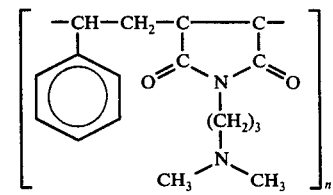

and copolymers of 2-vinyl and 2-methyl, 5-vinyl pyridines having the general formula

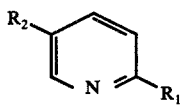

wherein R₁ is a methyl or vinyl group and R₂ is hydrogen or a vinyl group; and, c. electronic oscillator means operatively connected to said coated piezoelectric material for oscillating said material.

6. A process for the static detection and measurement of a sulfur dioxide component of a mixed gas stream comprising the following steps:

a. coating a vibrateable piezoelectric material with a polyamine substrate selected from the group consisting of 1:1 copolymers of styrene and N,N-dimethylaminopropyl maleimide having the general formula

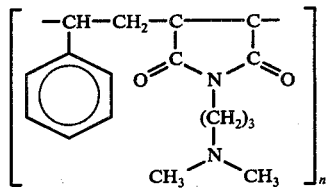

and copolymers of 2-vinyl and 2-methyl, 5-vinyl pyridines having the general formula

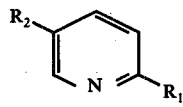

wherein R₁ is a methyl or vinyl group and R₂ is hydrogen or a vinyl group;

b. mounting said coated piezoelectric material on a readily-transportable support base and operatively connecting said coated piezoelectric material to electronic oscillator means for oscillating said material;

c. withdrawing a portion of said gas stream from said conduit and passing it into a test chamber;

d. sealing said test chamber by valve means so as to bring said portion of said gas stream into contact with said coated piezoelectric material under substantially static conditions; and, e. recording the frequency response of said coated piezoelectric material until the change in vibrational frequency is substantially complete.

7. The process of claim 6 wherein the concentration of sulfur dioxide is said gas stream is on the order of 1000 ppm. or less and said polyamine comprises substantially all of said substrate.

8. The process of claim 6 wherein the concentration of sulfur dioxide in said gas stream is greater than about 1000 ppm. and said substrate comprises polyamine dispersed as a solid solution in an inert matrix.

9. The process of claim 8 wherein said polyamine is dispersed in Carbowax 6000 in an amount of about 1–50 wt.-%.

* * * * *